United States Patent
Hatanaka

(10) Patent No.: US 9,921,418 B2
(45) Date of Patent: Mar. 20, 2018

(54) SPECTACLE LENS SUPPLY SYSTEM, PROGRAM THEREFOR, PRISM AMOUNT DETERMINATION DEVICE, PRISM AMOUNT DETERMINATION METHOD, AND METHOD FOR PRODUCING SPECTACLE LENS

(71) Applicant: HOYA LENS THAILAND LTD., Thanyaburi, Patumthani (TH)

(72) Inventor: Takashi Hatanaka, Tokyo (JP)

(73) Assignee: HOY A LENS THAILAND LTD., Thanyaburi (TH)

( * ) Notice: Subject to any disclaimer, the term of this patent is extended or adjusted under 35 U.S.C. 154(b) by 0 days.

(21) Appl. No.: 15/119,511

(22) PCT Filed: Feb. 19, 2015

(86) PCT No.: PCT/JP2015/054545
§ 371 (c)(1),
(2) Date: Aug. 17, 2016

(87) PCT Pub. No.: WO2015/125847
PCT Pub. Date: Aug. 27, 2015

(65) Prior Publication Data
US 2017/0199393 A1 Jul. 13, 2017

(30) Foreign Application Priority Data
Feb. 19, 2014 (JP) .................. 2014-029453

(51) Int. Cl.
*G02C 7/02* (2006.01)
*G02C 7/14* (2006.01)

(52) U.S. Cl.
CPC ............. *G02C 7/027* (2013.01); *G02C 7/025* (2013.01); *G02C 7/14* (2013.01); *G02C 2202/10* (2013.01)

(58) Field of Classification Search
USPC ....................... 351/159.7, 200-246
See application file for complete search history.

(56) References Cited

U.S. PATENT DOCUMENTS

| 6,048,064 A | 4/2000 | Hosoi et al. |
| 6,199,983 B1 | 3/2001 | Kato et al. |

(Continued)

FOREIGN PATENT DOCUMENTS

| JP | 2009-086568 A | 4/2009 |
| JP | 2010-052047 A | 3/2010 |
| JP | 2010-517088 A | 5/2010 |
| JP | 2012-085697 A | 5/2012 |
| WO | 2014/112626 A1 | 7/2014 |

OTHER PUBLICATIONS

May 19, 2015 International Search Report issued in International Patent Application No. PCT/JP2015/054545.

(Continued)

*Primary Examiner* — Mohammed Hasan
(74) *Attorney, Agent, or Firm* — Oliff PLC

(57) ABSTRACT

An aligning prism amount determination device to determine an aligning prism amount for correcting fixation disparity of a spectacle wearer, having the fixation disparity, includes a determiner to determine an aligning prism amount to be uniformly included in the spectacle lens for correcting the fixation disparity, based on a first aligning prism amount obtained by measuring an aligning prism amount of the spectacle wearer at an eye examination distance corresponding to a first distance, a second aligning prism amount obtained by measurement at an eye examination distance corresponding to a second distance shorter than the first distance, and information used for allocation of the first aligning prism amount and the second aligning prism amount, within a prism prescription range between the first aligning prism amount and the second aligning prism amount.

11 Claims, 4 Drawing Sheets

(56) References Cited

U.S. PATENT DOCUMENTS

| | | | | |
|---|---|---|---|---|
| 7,441,895 B2* | 10/2008 | Akiyama | ............... | A61B 3/10 |
| | | | | 351/178 |
| 8,295,961 B2* | 10/2012 | Daimaru | ............ | G02C 13/003 |
| | | | | 33/554 |
| 8,356,896 B2* | 1/2013 | Esser | ................. | A61B 3/0025 |
| | | | | 351/200 |
| 8,506,076 B2* | 8/2013 | Becken | ................. | G02C 7/02 |
| | | | | 351/159.73 |
| 8,511,826 B2* | 8/2013 | Ozaki | .................. | A61B 3/028 |
| | | | | 351/222 |
| 2006/0139571 A1 | 6/2006 | Poulain et al. | | |
| 2010/0296055 A1 | 11/2010 | Esser et al. | | |
| 2012/0092621 A1 | 4/2012 | Ozaki | | |

OTHER PUBLICATIONS

Mariko Takaki. "Prismotherapy in Middle Aged Patients With Diplopia". Japanese Orthoptic Journal, Aug. 2002, vol. 31, pp. 67-73.

Richard London et al. "Fixation Disparity Analysis: Sensory and Motor Approaches". Optometry, Dec. 2006, vol. 77, No. 12, pp. 590-608.

Sep. 12, 2017 Extended European Search Report issued in European Application No. 15751955.4.

* cited by examiner

| DISTANCE VISION | | NEAR VISION | |
|---|---|---|---|
| LIFE SCENE | IMPORTANCE INDEX | LIFE SCENE | IMPORTANCE INDEX |
| DRIVING (F1) | 2 | READING (N1) | 1 |
| OUTDOOR SPORTS (F2) | 0 | PC OPERATION (N2) | 1 |
| HIKING (F3) | 0 | COOKING (N3) | 2 |

FIG. 6

| | | | |
|---|---|---|---|
| DISTANCE VISION FIXATION DISPARITY AMOUNT | RIGHT: | 1.08 IN | 0.14 UP |
| | LEFT: | 1.08 IN | 0.14 DOWN |
| NEAR VISION FIXATION DISPARITY AMOUNT | RIGHT: | 1.46 IN | 0.31 UP |
| | LEFT: | 1.46 IN | 0.31 DOWN |

31

32 (min.)

SPECTACLE LENS SUPPLY SYSTEM, PROGRAM THEREFOR, PRISM AMOUNT DETERMINATION DEVICE, PRISM AMOUNT DETERMINATION METHOD, AND METHOD FOR PRODUCING SPECTACLE LENS

TECHNICAL FIELD

The present invention relates to a spectacle lens supply system, a program therefor, a prism amount determination device, a prism amount determination method, and a method for producing a spectacle lens.

BACKGROUND ART

One of items to be corrected by a spectacle lens includes "fixation disparity". Fixation disparity refers to a state where, when both eyes simultaneously look at (fixate) an object, one of or both of the eyes cannot form an image at a position of the central fovea of retina and the image is formed at a position slightly shifted from the central fovea. Fixation disparity occurs due to a shift in a sight line. Therefore, when a person with fixation disparity sees the same object by binocular vision, a position of forming an image when the object is seen with the left eye and a position of forming an image when the object is seen with the right eye are slightly shifted from the central fovea of the left and the right eyes, respectively. However, the shift in positions of forming images due to fixation disparity is quite small such as several minutes in the sight line angle and thus fusion of images in the brain results in perception of the images as one image. Therefore, the image of the right eye and the image of the left eye are not perceived as shifted in a binocular vision and a blur of images is rarely recognized. However, since the position of forming the image of each of the left and the right eyes is shifted from the central fovea thereof, a vision with the both eyes is deteriorated and a vision with the both eyes becomes unstable. However, this is rarely recognized by the person.

Moreover, a person having fixation disparity often feels physical pain such as fatigue of the eyes, headache, or shoulder stiffness. Checking a cause of the above by testing at a hospital or the like may clarify that the person has fixation disparity. In this case, in order to relieve the pain caused by fixation disparity, it is desirable to measure a prism amount, where a given prism exactly eliminates the fixation disparity, using a plurality of test lenses having different prism powers and to wear a spectacle lens prescribed a prism (prism correction) in accordance with this prism amount. As for the prism amount, a technique described in Patent Literature 1 is known for example. In this manner, the prism amount where the fixation disparity of the spectacle wearer is exactly eliminated is called an aligning prism.

CITATION LIST

Patent Literature

Patent Literature 1: JP 2010-052047 A

SUMMARY OF INVENTION

Technical Problem

Meanwhile, measurement of an aligning prism amount required for correcting fixation disparity (hereinafter, simply referred to as a "prism amount" for convenience of description) may be performed with distance vision or near vision depending on a difference in distance from a position of the eye of a subject of an eye examination to an optotype for measurement (hereinafter, also referred to as an "eye examination distance"). Moreover, measurement of the aligning prism amount is performed at an optician's store or an ophthalmological clinic. In this case, the prism amount is measured with one of distance vision or near vision at the optician's store or the like and the prism amount obtained from the measurement is transmitted to a lens manufacturer or the like as a prescribed prism amount, thereby ordering a spectacle lens with prism prescription.

Generally, however, the aligning prism amount measured with distance vision and the aligning prism amount measured with near vision result in different values even with the same subject. This is because the both eyes converge inward for near vision and the eyes are adjusted according to a near distance and thus circumstances where an object is seen are different between near vision and distance vision. Therefore, a state of fixation disparity is different between distance vision and near vision, which often results in different prism amounts for correcting fixation disparity between distance vision and near vision. Therefore, a spectacle lens with prism prescription in accordance with the aligning prism amount measured with distance vision cannot appropriately correct fixation disparity of near vision. Contrary to this, a spectacle lens with prism prescription in accordance with the aligning prism amount measured with near vision cannot appropriately correct fixation disparity of distance vision.

A main object of the present invention is to provide a technique capable of correcting fixation disparity with a prescribed prism amount more suitable for a spectacle wearer of a spectacle lens than before.

Solution to Problem

A countermeasure against the above issue may be, for example, adjusting a value of a prescribed prism amount according to an object of a spectacle wearer to use a spectacle lens without using an aligning prism amount measured with distance vision as the prescribed prism amount as it is. In such a countermeasure, however, how much to adjust the value of the prescribed prism amount is determined by a sense or experience of a store clerk at an optician's store or the like. Therefore, a spectacle lens with prism prescription according to the spectacle wearer's preference cannot always be provided.

Furthermore, as another countermeasure, an aligning prism amount measured with distance vision may be applied to a distance portion of the spectacle lens while an aligning prism amount measured with near vision may be applied to a near portion of the spectacle lens, that is, to allow one spectacle lens to include two prism amounts. However in this case, generation of a level difference between the distance portion and the near portion cannot be avoided. This results in jumping of images when a sight line moves from distance vision to near vision, thereby significantly deteriorating a vision.

The present inventor therefore devised a method to measure aligning prism amounts of the spectacle wearer separately at an eye examination distance corresponding to distance vision and at an eye examination distance corresponding to near vision, to thereby obtain a first prism amount and a second prism amount, and to determine a prescribed prism amount within a prism prescription range between the first prism amount and the second prism amount based on information related to life scenes of the spectacle wearer with respect to how the spectacle wearer uses spectacles in what way of life. Also devised is the method further to apply this prescribed prism amount uniformly to a spectacle lens. A finding has been obtained that, with this method, the prescribed prism amount is determined with the prism amount more suitable for the spectacle wearer than before and fixation disparity of the spectacle wearer is corrected according to this prescribed prism amount.

Aspects of the invention devised based on the above finding are as follows.

A first aspect of the present invention is a spectacle lens supply system to supply a spectacle lens for correcting fixation disparity of a spectacle wearer, of a spectacle lens, having the fixation disparity, the system including a determination section to determine an aligning prism amount to be uniformly included in the spectacle lens for correcting the fixation disparity, based on a first aligning prism amount obtained by measurement at an eye examination distance corresponding to a first distance, a second aligning prism amount obtained by measurement at an eye examination distance corresponding to a second distance shorter than the first distance, and information used for allocation of the first aligning prism amount and the second aligning prism amount, within a prism prescription range between the first aligning prism amount and the second aligning prism amount.

A second aspect of the present invention is the spectacle lens supply system according to the first aspect, where the information used for allocation of the first aligning prism amount and the second aligning prism amount relates to a life scene where the spectacle wearer plans to use the spectacle lens.

A third aspect of the present invention is the spectacle lens supply system according to the second aspect, the system including a measurement information input section to input the first aligning prism amount and the second aligning prism amount and a life scene information input section to input the information related to the life scene.

A fourth aspect of the present invention is the spectacle lens supply system according to the third aspect, the system further including a display to display an input screen for inputting the first aligning prism amount and the second aligning prism amount.

A fifth aspect of the present invention is the spectacle lens supply system according to the third or fourth aspect, where the life scene information input section inputs information representing an importance index based on a life style of the spectacle wearer for each of a plurality of life scenes prepared in advance and the determination section obtains allocation within the prism prescription range using the importance index for each of the plurality of life scenes input by the input section and determines an aligning prism amount for correcting the fixation disparity according to this allocation.

A sixth aspect of the present invention is the spectacle lens supply system according to any one of the third to fifth aspects, where the life scene information input section inputs, as the information related to the life scene, a coefficient K (where $0 \leq K \leq 1.0$ is satisfied) corresponding to a life style of the spectacle wearer and the determination section determines an aligning prism amount for correcting the fixation disparity from the following formula 1 where a prism amount in a horizontal direction of the aligning prism amount for correcting the fixation disparity is denoted as APLH, a prism amount in a vertical direction thereof is denoted as APLV, a prism amount in the horizontal direction of the first aligning prism amount is denoted as APF0H, a prism amount in the vertical direction of the first aligning prism amount is denoted as APF0V, a prism amount in the horizontal direction of the second aligning prism amount is denoted as APN0H, and a prism amount in the vertical direction of the second aligning prism amount is denoted as APN0V.

$$APLH = APF0H*(1-K) + APN0H*K$$

$$APLV = APF0V*(1-K) + APN0V*K \quad \text{[Formula 1]}$$

A seventh aspect of the present invention is the spectacle lens supply system according to any one of the first to sixth aspects, where the first distance is an eye examination distance corresponding to distance vision and the second distance is an eye examination distance corresponding to near vision.

An eighth aspect of the present invention is a non-transitory computer-readable recording medium storing a program for a spectacle lens supply system to cause a computer of an aligning prism amount determination device to determine an aligning prism amount for correcting fixation disparity of a spectacle wearer, of a spectacle lens, having the fixation disparity to function as:

a determination section to determine an aligning prism amount for correcting the fixation disparity, when a first aligning prism amount obtained by measurement at an eye examination distance corresponding to a first distance, a second aligning prism amount obtained by measurement at an eye examination distance corresponding to a second distance shorter than the first distance, and information used for allocation of the first aligning prism amount and the second aligning prism amount are input, based on the input information within a prism prescription range between the first aligning prism amount and the second aligning prism amount.

A ninth aspect of the present invention is a method for producing a spectacle lens for correcting fixation disparity of a spectacle wearer, of a spectacle lens, having the fixation disparity, the method including the steps of: determining an aligning prism amount for correcting the fixation disparity, based on a first aligning prism amount obtained by measurement at an eye examination distance corresponding to a first distance, a second aligning prism amount obtained by measurement at an eye examination distance corresponding to a second distance shorter than the first distance, and information used for allocation of the first aligning prism amount and the second aligning prism amount, within a prism prescription range between the first aligning prism amount and the second aligning prism amount; and producing a spectacle lens uniformly including the determined aligning prism amount for correcting the fixation disparity.

A tenth aspect of the present invention is a prism amount determination device to determine a prism amount for correcting fixation disparity of a spectacle wearer, of a spectacle lens, having the fixation disparity, the device including a determination section to determine an aligning prism amount to be uniformly included in the spectacle lens for correcting the fixation disparity, based on a first aligning prism amount obtained by measurement at an eye examination distance corresponding to a first distance, a second aligning prism amount obtained by measurement at an eye examination distance corresponding to a second distance shorter than the first distance, and information used for allocation of the first aligning prism amount and the second aligning prism amount, within a prism prescription range between the first aligning prism amount and the second aligning prism amount.

An eleventh aspect of the present invention is a prism amount determination method to determine an aligning prism amount for correcting fixation disparity of a spectacle wearer, of a spectacle lens, having the fixation disparity, the method including the step of: determining an aligning prism amount for correcting the fixation disparity, based on a first aligning prism amount obtained by measurement at an eye examination distance corresponding to a first distance, a second aligning prism amount obtained by measurement at an eye examination distance corresponding to a second distance shorter than the first distance, and information used for allocation of the first aligning prism amount and the second aligning prism amount, within a prism prescription range between the first aligning prism amount and the second aligning prism amount.

Advantageous Effects of Invention

The present invention allows for correcting fixation disparity with a prism amount more suitable for a spectacle wearer of a spectacle lens than before.

BRIEF DESCRIPTION OF DRAWINGS

FIG. 6 is a diagram illustrating exemplary display of an input screen for inputting a first fixation disparity amount and a second fixation disparity amount.

DESCRIPTION OF EMBODIMENTS

Hereinafter, an embodiment of the present invention will be described in detail with reference to the drawings.

The embodiment of the present invention will be described in the following order.
1. Configuration of Spectacle Lens Supply System
2. Configuration of Order Placing Device
3. Procedure of Lens Order Placing Processing Including Prism Amount Determination Method
4. Effects of Embodiment
5. Other Embodiments
6. Variations 1. Configuration of Spectacle Lens Supply System FIG. 1 a schematic diagram illustrating an exemplary configuration of a spectacle lens supply system according to an embodiment of the present invention.

Figure 1:
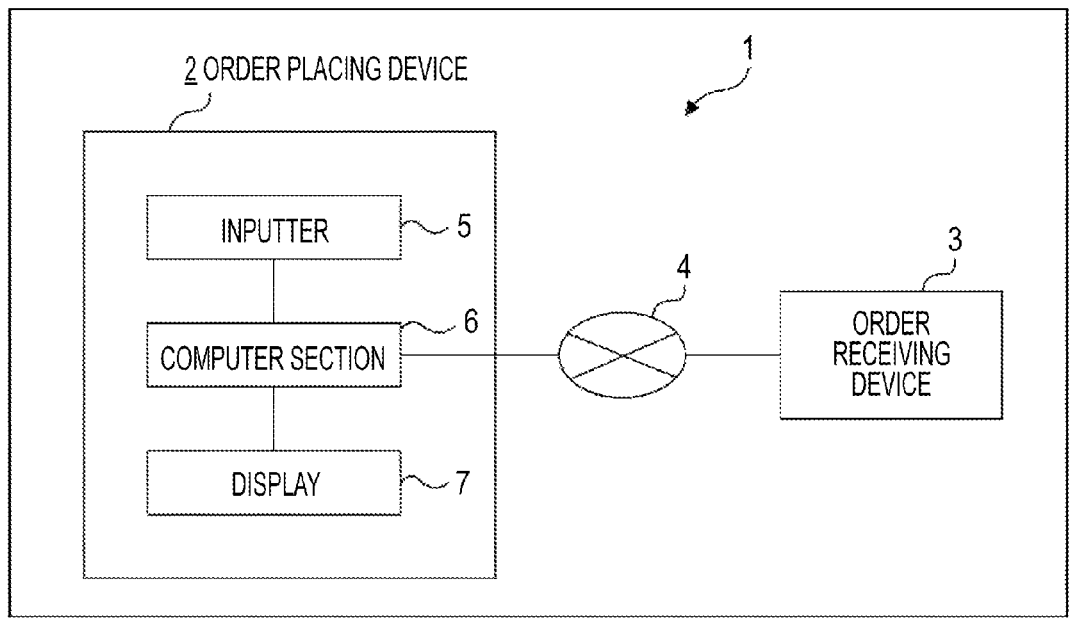
FIG. 1 is a schematic diagram illustrating an exemplary configuration of a spectacle lens supply system according to an embodiment of the present invention.

A spectacle lens supply system 1 illustrated in FIG. 1 has a configuration where an order placing device 2 and an order receiving device 3 are connected, to allow communication therebetween, by a communication network 4. The order placing device 2 is used while, for example, installed at an optician's store and the order receiving device 3 is used while, for example, installed at a production facility of spectacle lenses or the like. The communication network 4 includes, for example, the Internet, a dedicated line, or the like. In this spectacle lens supply system 1, information required for placing an order for a spectacle lens is transmitted to the order receiving device 3 via the communication network 4. Furthermore in the order receiving device 3, required lens processing is performed using the received information. The spectacle lens ultimately determined as a conforming article after testing or the like is supplied to the optician's store which has placed the order. The lens processing includes, for example, polishing processing of an optical surface of the lens and lens shape processing for fitting into a frame.

In the spectacle lens supply system 1 configured as above, correspondence relation between the order placing device 2 and the order receiving device 3 may be any one of correspondence relation of 1:1, correspondence relation of m:1 (where m is a natural number of 2 or more), correspondence relation of 1:n (where n is a natural number of 2 or more), and correspondence relation of m:n. Moreover, the order placing device 2 and the order receiving device 3 may be installed in the same country or in different countries. Although not illustrated, various servers (e.g. data server) may be connected to the communication network 4 and the server and the order placing device 2 or the order receiving device 3 may exchange data as required.

2. Configuration of Order Placing Device

The order placing device 2 is provided as an exemplary "prism amount determination device" according to the embodiment of present invention. The order placing device 2 is configured by hardware resources of a computer and includes an inputter 5, a computer section 6, and a display 7. The inputter 5 inputs various data (information) to the order placing device 2. The inputter 5 can be configured by an input operation device such as a keyboard, a mouse, and a touch panel or an input/output interface or the like to accept data input from a portable terminal or a portable storage device (e.g. USB memory). The inputter 5 includes a "measurement information input section" and a "life scene information input section" of the embodiment of the present invention. Measurement information input by the measurement information input section includes a first prism amount obtained by measurement of an aligning prism amount of a spectacle wearer at an eye examination distance corresponding to distance vision and a second prism amount obtained by measurement at an eye examination distance corresponding to near vision. Furthermore, life scene information input by the life scene information input section includes information related to a life scene where the spectacle wearer plans to use the spectacle lens. Details of each piece of information will be described later.

The display 7 displays various information to a spectacle wearer wearing or planning to wear a spectacle lens (hereinafter, also simply referred to as a "spectacle wearer") or to a store clerk at an optician's store. The display 7 may be configured by, for example a liquid crystal display device or an organic EL display device.

(Computer Section)

The computer section 6 is configured by a central processing unit (CPU), a read only memory (ROM), a random access memory (RAM), a hard disk drive (HDD), or the like that are a part of hardware resources of a computer.

Figure 2:
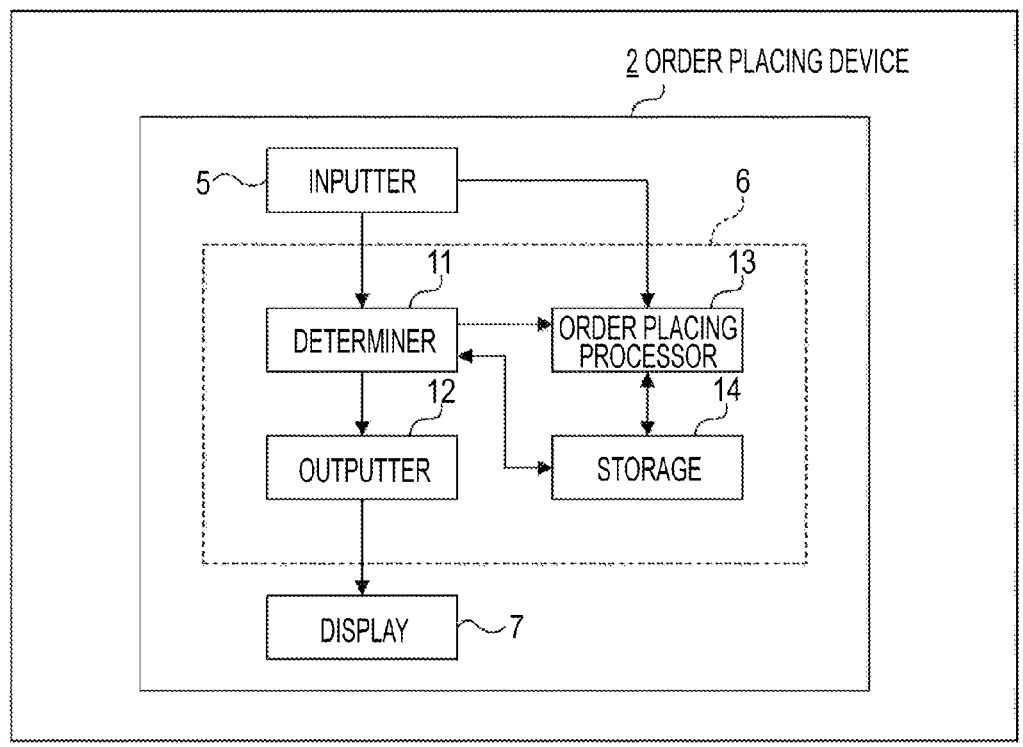
FIG. 2 is a schematic diagram illustrating an exemplary configuration of an order placing device according to the embodiment of the present invention.

The computer section 6 includes a determiner 11, an outputter 12, an order placing processor 13, and a storage 14 as illustrated in FIG. 2. Each of the functional sections is implemented by the aforementioned hardware resources of a computer. Each of the aforementioned functional sections of the computer section 6 is implemented when, for example, a CPU reads a program stored in a ROM or an HDD to a RAM and executing the program. In this case, the program can be extracted as one aspect of the present invention.

(Determiner)

The determiner 11 determines a prescribed prism amount based on the various information input by the inputter 5. The prescribed prism amount refers to a prism amount applied to prescription of a spectacle lens when a spectacle wearer with fixation disparity corrects the fixation disparity by wearing the spectacle lens, that is, an aligning prism amount for correcting the fixation disparity. A value of the prescribed prism amount for a spectacle wearer without fixation disparity equals zero while a value (absolute value) of the prescribed prism amount for a spectacle wearer with fixation disparity is larger than zero. Moreover, a spectacle lens prescribed a prism according to the prescribed prism amount results as a lens incorporated with the prism according to the prescribed prism amount (prism lens). This prism amount is to be uniformly applied to a lens. This can avoid forming a level difference between the distance portion and the near portion of the spectacle lens.

Incidentally, as the above fixation disparity, fixation disparity obtained by a known measurement may be used.

(Outputter)

The outputter 12 outputs a type of spectacle lens recommended to a spectacle wearer. A specific output mode may be display output, printout, voice output or the like. Moreover, a target for the outputter 12 to output a recommended type (output destination) may be the display 7 for example. In the embodiment of the present invention, the recommended type of spectacle lens is output as a display on a screen of the display 7 by a text, an illustration, a picture, an image, a video (moving image), or the like according to an output instruction from the outputter 12.

(Order Placing Processor)

The order placing processor 13 performs order placing processing of a spectacle lens. Specifically, the order placing processor 13 performs processing of extracting information required for placing an order for the spectacle lens from the information input by the inputter 5 and transmitting this information to the order receiving device 3 via the communication network 4. The order placing processor 13 further performs processing of transmitting, to the order receiving device 3 via the communication network 4, information (manufacturer, type, etc.) to specify the recommended type of spectacle lens ultimately determined (confirmed) by the store clerk at the optician's store with a consent of the spectacle wearer.

(Storage)

The storage 14 is used for storing various data handled in the order placing device 2. The data stored in the storage 14 includes the first prism amount, the second prism amount, and the information related to the life scene of the spectacle wearer input by the inputter 5. These pieces of information are referred to when the determiner 11 determines the aligning prism amount for correcting the fixation disparity.

Figure 3:
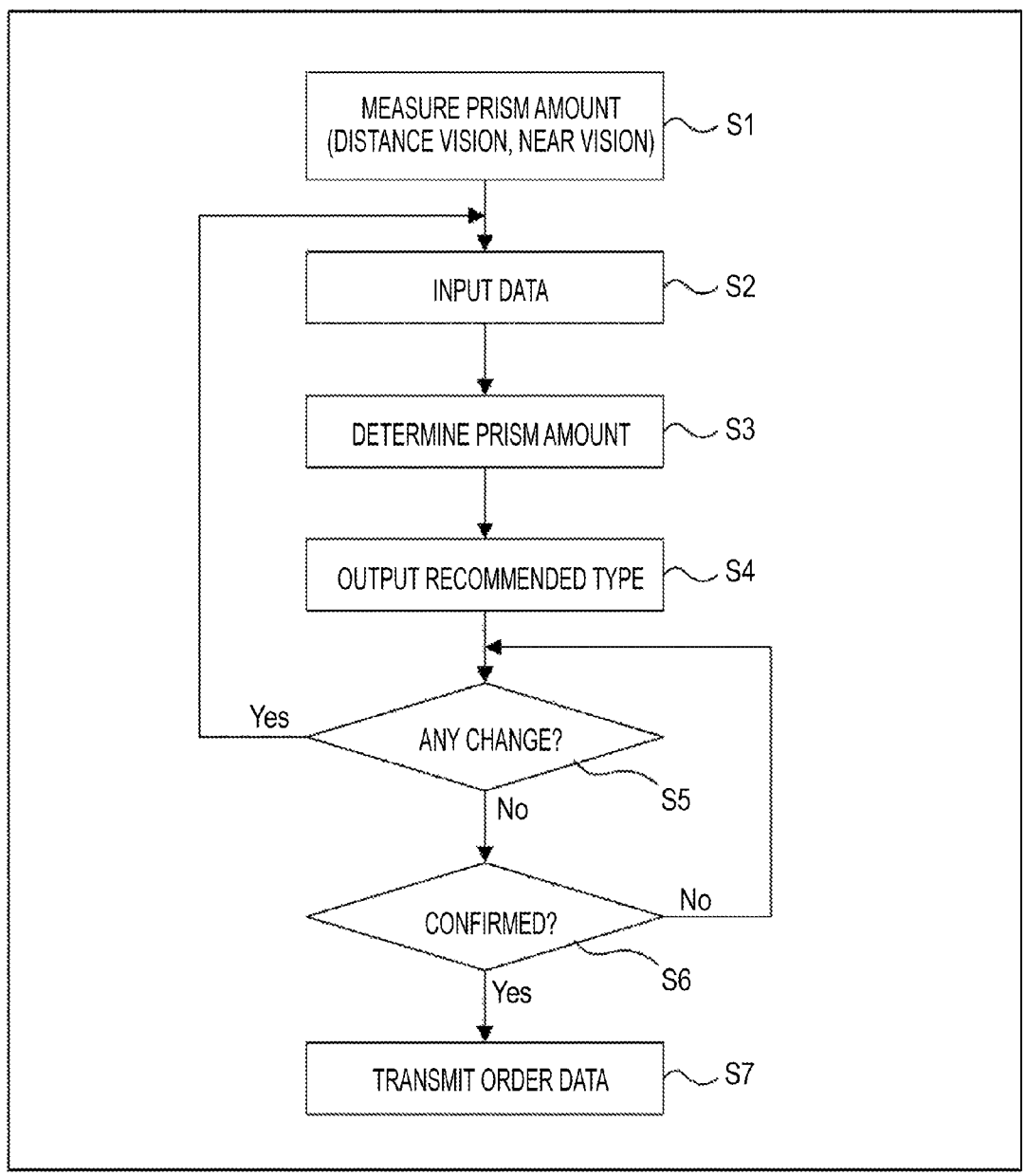
FIG. 3 is a flowchart illustrating a procedure of lens order placing processing including a prism amount determination method according to the embodiment of the present invention.

3. Procedure of Lens Order Placing Processing Including Prism Amount Determination Method FIG. 3 is a flowchart illustrating a procedure of lens order placing processing including a prism amount determination method according to the embodiment of the present invention.

(Measurement of Prism Amount)

First, an aligning prism amount for correcting fixation disparity of a spectacle wearer of a spectacle lens is measured (S1). The prism amount described herein does not include a prism amount of a spectacle lens measured using a lens meter or the like but includes a prism amount obtained by performing an eye examination with the spectacle wearer wearing or planning to wear a spectacle lens as a subject. As for the measurement of the aligning prism amount for correcting fixation disparity of the spectacle wearer, a known measurement method may be used. One of known measurement methods will be described below.

First, a plurality of test lenses having different prism powers is used for measurement of the aligning prism amount for correcting fixation disparity of the spectacle wearer. Each of the test lenses is formed in a freely detachable manner from a test frame. Therefore, an optotype used for measurement of the aligning prism amount for correcting fixation disparity is shown to the spectacle wearer while the test lens to mount to the test frame is changed as appropriate. This optotype includes an optotype to be presented to both of the left and the right eyes and an optotype to be separately presented to the left and the right eyes. For separately presenting the optotype to the left and the right eyes, there is a method using a computer display capable of stereoscopic display that can present different images to the left and the right eyes. As for a method to separately presenting the optotype to the left and the right eyes in an easy manner, there is a method to present an optotype commonly presented to the left and the right eyes in black while presenting an optotype presented only to the right eye in green and presenting an optotype presented only to the left eye in red with a red color filter mounted on a right eye side of the test frame and a green color filter mounted on a left eye side thereof. In this case, the optotype presented only to the right eye is presented in green and seeing this optotype through the red color filter mounted on the right eye side results in black color to the eye. On the other hand, the green color filter is mounted on the left eye side and thus the optotype presented only to the right eye that is presented in green cannot be distinguished from a background color of white or pale grey and thus is invisible to the eye. Here, the optotypes appear differently depending on whether the spectacle wearer has fixation disparity. That is, when a person without fixation disparity sees the optotypes through the test lens without a prism power, the spectacle wearer sees the optotypes at original positions. In this case, the prism amount of the spectacle wearer is measured as substantially zero. Contrary to this, when a person with fixation disparity sees the optotypes through the test lens without a prism power, the spectacle wearer cannot see the optotypes separately presented to the left and the right eyes at original positions but at positions shifted therefrom. In this case, how the optotypes appear is confirmed using some of the test lenses and specifies the test lens that allows the spectacle wearer with fixation disparity to see the optotypes at the original positions. Thereafter, a prism power of the specified test lens is read as a prism amount of the spectacle wearer. Measurement of the prism amount is performed for each of the horizontal direction (leftward/rightward direction) and the vertical direction (upward/downward direction).

In the embodiment of the present invention, measurement of the aligning prism amount for correcting fixation disparity as exemplified above is performed in two steps. First, in a first step, an aligning prism amount of the spectacle wearer is measured at an eye examination distance corresponding to distance vision, thereby obtaining a first prism amount. The eye examination distance refers to a distance (direct distance) from a position of the eyes of a subject to the optotype used for measurement of the aligning prism amount. The eye examination distance corresponding to distance vision refers to a distance where the subject sees the optotype used for measurement of the aligning prism amount with both of the eyes and the subject can see the optotype with sight lines of the both eyes substantially parallel to each other, which is a distance within a range of approximately 3 to 6 m. Measuring a prism amount of the spectacle wearer at such an eye examination distance results in obtaining the aforementioned first prism amount. Here, the aligning prism amount is measured separately for a prism in the horizontal direction and a prism in the vertical direction. In descriptions below, a prism amount in the horizontal direction and a prism amount in the vertical direction of the first prism amount are denoted as APF0H and APF0V, respectively.

Next, in a second step, an aligning prism amount for correcting fixation disparity of the spectacle wearer is measured at an eye examination distance corresponding to near vision, thereby obtaining a second prism amount. The eye examination distance corresponding to near vision refers to a distance where the subject sees the optotype used for measurement of the aligning prism amount with both of the eyes and the subject sees the optotype with sight lines of the both eyes directed inward to each other (inclined toward each other), which is a distance within a range of approximately 30 to 50 cm. The eye examination distance corresponding to near vision is shorter than the aforementioned eye examination distance corresponding to distance vision. Measuring a prism amount of the spectacle wearer at such a short eye examination distance results in obtaining the second prism amount. Here, the aligning prism amount is measured separately for a prism in the horizontal direction and a prism in the vertical direction. In descriptions below, a prism amount in the horizontal direction and a prism amount in the vertical direction of the second prism amount are denoted as APN0H and APN0V, respectively. Note that, when the spectacle wearer has presbyopia, it is desirable to perform measurement at the eye examination distance corresponding to near vision while a necessary power for near vision is included.

(Data Input)

Figures 4, 5:
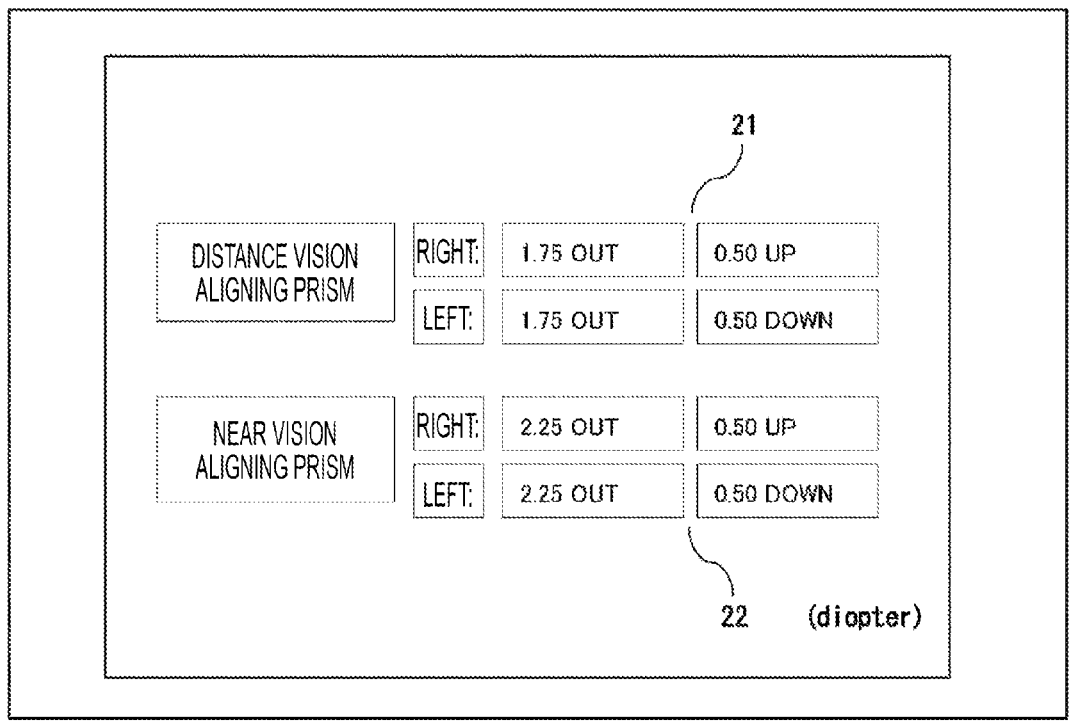
FIG. 4 is a diagram illustrating an example where an importance index based on a life style of a spectacle wearer is input for each life scene.
FIG. 5 is a diagram illustrating exemplary display of an input screen for inputting a first prism amount and a second prism amount.

Next, the respective values of the first prism amounts APF0H and APF0V and the second prism amounts APN0H and APN0V obtained from the above measurement are subjected to data input from the inputter 5 of the order placing device 2 together with other information required for ordering a spectacle lens (e.g. addition power of the spectacle lens (distance power, near power), lens prescription information including an astigmatic axis or the like, frame information including a type, a material, a size, frame shape data, etc. of a spectacle frame, or layout information used for aligning the spectacle lens and the spectacle frame) (S2). Usually, an aligning prism for correcting fixation disparity is measured separately with respect to a prism in the horizontal direction and a prism in the vertical direction and each of the prism amounts is further divided into two for the left eye and the right eye. For the prism in the horizontal direction, a prism value is added with a symbol representing a direction of IN or OUT and, for the prism in the vertical direction, a prism value is added with a symbol representing a direction of UP or DOWN, thereby distinguishing a direction of the prism. As an example, data input of the prism amount will be described. Data input of the prism amount may be performed by, for example displaying an input screen as illustrated in FIG. 5 on the display 7, thereby allowing an operator (store clerk at an optician's store or the like) to select entry fields 21 and 22 for the prism amount with a mouse or the like in order while looking at this input screen and to input a corresponding prism value and the symbol representing the direction with a keyboard or the like. A distance vision prism amount in FIG. 5 corresponds to the first prism amount APF0 obtained by measuring the prism amount of the spectacle wearer at the eye examination distance corresponding to distance vision and a near vision prism amount in FIG. 5 corresponds to the second prism amount APN0 obtained by measuring the prism amount of the spectacle wearer at the eye examination distance corresponding to near vision. Here, when measurement of the prism amount required for data input is performed at a location away from the optician's store, a measurement result may be notified from the measurement location to a communication device of the optician's store by a communication means such as facsimile or email before the date input.

The information related to life scenes where the spectacle wearer plans to use the spectacle lens is further input from the inputter 5. Specifically, information representing the importance index based on a life style of the spectacle wearer is input for each of the plurality of life scenes prepared in advance. In the embodiment of the present invention, information representing the importance index based on a life style of the spectacle wearer is input for each of six life scenes described in (1) to (6) below as an example (see FIG. 4).

(1) Scene of Driving Car
(2) Scene of Playing Outdoor Sports (Tennis, Skiing, etc.)
(3) Scene of Hiking (Walking)
(4) Scene of Beading
(5) Scene of Operating Personal Computer
(6) Scene of Cooking Of these, (1) to (3) are life scenes where an object is mainly looked at by distance vision and (4) to (6) are life scenes where an object is mainly looked at by near vision. It is preferable that the number of life scenes prepared in advance is substantially the same for distance vision and near vision.

Furthermore, the importance index based on a life style of the spectacle wearer is classified into three ranks of "0 (low)", "1 (intermediate)", and "2 (high)" according to a level of importance thereof for each of the aforementioned six life scenes and one of the indices is input. As for which index to actually input, the store clerk at the optician's store or the like may confirm the life style with the spectacle wearer in a questionnaire form or the like and thereby determine based on this confirmation result. For example for the above scene of reading of (3), the importance index is input based on determination criteria as the following. That is, when reading is one of hobbies of the spectacle wearer and the spectacle wearer has many chances of reading while wearing a spectacle lens on a daily basis, the importance index of "2" is input. Alternatively, even if reading is one of hobbies, when the spectacle wearer reads a book only occasionally, the importance index of "1" is input while the importance index of "0" is input for other spectacle wearers (those seldom read a book).

Inputting various data (information) from the inputter 5 in the above manner allows the computer section 6 to perform the following processing using this input data.

(Determination of Prism Amount)

That is, the determiner 11 determines the aligning prism amount for correcting fixation disparity using the data input from the inputter 5 (step S3). A prism amount in the horizontal direction and a prism amount in the vertical direction of the aligning prism amount for correcting the fixation disparity (hereinafter, also simply referred to as a "prescribed prism amount") are denoted as APLH and APLV, respectively. The determiner 11 determines a prescribed prism amount in the horizontal direction APLH within a prism prescription range between the first prism amount in the horizontal direction APF0H and the second prism amount in the horizontal direction APN0H and also determines a prescribed prism amount in the vertical direction APLV within a prism prescription range between the first prism amount in the vertical direction APF0V and the second prism amount in the vertical direction APN0V. The prism prescription range refers to a range of prism amount from the minimum value to the maximum value (including the minimum value and the maximum value), where the prism amount relatively larger than the other, of the prism amounts in each of the horizontal direction and the vertical direction of the first prism amounts APF0H and APF0V and the second prism amounts APN0H and APN0V, is regarded as the maximum value while the other smaller prism amount is regarded as the minimum value. Within the prism prescription range in each of the horizontal direction and the vertical direction, allocation (described later) within the prism prescription range is obtained using the importance index for each of the aforementioned plurality of life scenes. The prescribed prism amounts APLH and APLV in the horizontal direction and the vertical direction, respectively, are determined according to this allocation. Hereinafter, an exemplary method to determine the prescribed prism amounts APLH and APLV using a specific mathematical formula will be described.

First, as a premise of description, of the aforementioned six life scenes, the importance indices (0, 1, 2) are input as F1, F2, and F3 for the life scenes where an object is mainly looked at by distance vision while the importance indices are input as N1, N2, and N3 for the life scenes where an object is mainly looked at by near vision. In this case, the determiner 11 determines the prescribed prism amounts APLH and APLV based on the following formula 2.

$$KF=(F1+F2+F3)/(F1+F2+F3+N1+N2+N3)$$

$$KN=(N1+N2+N3)/(F1+F2+F3+N1+N2+N3) \quad \text{[Formula 2]}$$

$$APF1H=APF0H*KF$$

$$APF1V=APF0V*KF$$

$$APN1H=APN0H*KN$$

$$APN1V=APN0V*KN$$

$$APLH=APF1H+APN1H$$

$$APLV=APF1V+APN1V$$

Note that the aforementioned allocation within the aforementioned prism prescription range means a value of coefficient KF representing a ratio of weighting of the first prism amounts APF0H and APF0V measured with distance vision as well as a value of coefficient KN representing a ratio of weighting of the second prism amounts APN0H and APN0V measured with near vision when the prescribed prism amounts APLH and APLV are determined within the prism prescription range. In the example illustrated in FIG. 4, KF=1/3 and KN=2/3. Therefore, when the prism amount in the horizontal direction of the first prism amount APF0H is 3Δ (prism diopter) and the prism amount in the horizontal direction of the second prism amount APN0H is 2Δ, a value of APF1H equals 3/3 and a value of APN1H equals 4/3. As a result, a value of the prescribed prism amount in the horizontal direction APLH is calculated as 7/3. Therefore, when the prism amount in the vertical direction of the first prism amount APF0V is 1Δ (prism diopter) and the prism amount in the vertical direction of the second prism amount APN0V is 1.5Δ, a value of APF1V equals 1/3 and a value of APN1V equals 3/3. As a result, a value of the prescribed prism amount in the vertical direction APLV is calculated as 4/3. In production of spectacle lenses, when a possible value as a prescribed prism amount is within a certain range, a value closest to the values of APLH and APLV calculated within the range may be determined as the prescribed prism amount. In ordering a spectacle lens, each of the prescription prisms in the horizontal direction and the vertical direction obtained in the above manner are respectively divided into a prescription prism value for the right eye and a prescription prism value for the left eye and thereby an order is placed. This is a common practice among ophthalmologists, optician's stores, and spectacle lens manufacturers.

(Output of Recommended Type)

Next, the outputter 12 outputs a type of spectacle lens recommended to the spectacle wearer based on the data input from the inputter 5 (S4). Specifically, in order to present a recommended type of spectacle lens to the spectacle wearer, the recommended type is output as a display on the screen of the display 7 by a text, an illustration, or the like. Contents output as the recommended type of spectacle lens include at least information related to a type of spectacle lens (lens for myopia, lens for presbyopia, distance-near vision lens, lens for astigmatism, spherical lens, aspherical lens, etc.). Other than the above, information related to a prescribed power, a prescribed prism amount, a lens material, a lens thickness, or the like of the spectacle lens may also be output as required.

(Order Placing Processing)

Next, the order placing processor 13 confirms whether operation to change the recommended type of spectacle lens displayed on the display 7 has been performed in the inputter 5 (S5). When this operation has been performed, the data input of the step S2 is performed once again and then a prism amount is determined and the recommended type is output.

Next, the order placing processor 13 confirms whether operation to confirm the order for the recommended type of spectacle lens displayed on the display 7 has been performed in the inputter 5 (S6). When this operation has been performed, order data of the spectacle lens is transmitted to the order receiving device 3 via the communication network 4 (S7). Here, if the spectacle wearer has fixation disparity, values of the prescribed prism amounts APLH and APLV in the horizontal direction and the vertical direction, respectively, required for correcting the fixation disparity is transmitted from the order placing device 2 to the order receiving device 3 as information of prescription values. Therefore, the spectacle lens supplied from the order receiving device 3 to the order placing device 2 results as a lens with prism prescription based on the prescribed prism amounts APLH and APLV in the horizontal direction and the vertical direction, respectively, of the spectacle wearer.

(Production of Spectacle Lens)

Thereafter, an order receiving side produces a spectacle lens uniformly including the aligning prism amount for correcting the fixation disparity which has been determined. Incidentally, as for the method for production, a known method may be used.

4. Effects of Embodiment

According to the embodiment of the present invention, the aligning prism amount for correcting fixation disparity of the spectacle wearer is measured separately at the eye examination distance corresponding to distance vision and at the eye examination distance corresponding to near vision and the first prism amount in the horizontal direction APF0H, the first prism amount in the vertical direction APF0V, the second prism amount in the horizontal direction APN0H, and the second prism amount in the vertical direction APN0V are thereby obtained. The prescribed prism amount in the horizontal direction APLH and the prescribed prism amount in the vertical direction APLV are then determined based on the information related to the life scene within the prism prescription range between the first prism amount in the horizontal direction APF0H and the second prism amount in the horizontal direction APN0H and within the prism prescription range between the first prism amount in the vertical direction APF0V and the second prism amount in the vertical direction APN0V, respectively. This allows for determining the prescribed prism amounts APLH and APLV with the prism amount more suitable for the spectacle wearer than before and correcting fixation disparity of the spectacle wearer according to these prescribed prism amounts APLH and APLV. Hereinafter, technical grounds of the above will be described with examples.

Generally, when an aligning prism amount for correcting fixation disparity is measured with a person with fixation disparity as a subject, the aligning prism amounts obtained from the measurement is different between measurement performed at the eye examination distance corresponding to distance vision and measurement performed at the eye examination distance corresponding to near vision. In the related art, an aligning prism amount is measured with one of distance vision and near vision and a prescribed prism amount is determined based on a measurement result thereof. Therefore, for example when the aligning prism amount measured with distance vision is determined as the prescribed prism amount as it is, a spectacle lens may not have appropriate prism prescription for a spectacle wearer having many chances of wearing the spectacle lens with near vision or intermediate vision. Supposing that a store clerk at an optician's store confirms for what use the spectacle wearer uses the spectacle lens and the prescribed prism amount is artificially adjusted based on this result, appropriately handling this is difficult. Reasons for this are as follows. That is, measurement of the aligning prism amount by only one of distance vision and near vision cannot show size relation between the aligning prism amount measured with distance vision and the aligning prism amount measured with near vision. Therefore, a type of adjustment (adding or reducing), of the aligning prism amount of distance vision obtained by the measurement which results in a prescribed prism amount suitable for the spectacle wearer, cannot be specified. Moreover, even if there is a certain tendency in the size relation between the aligning prism amount measured with distance vision and the aligning prism amount measured with near vision, there are individual variations in an actual level of a difference therebetween. Therefore, appropriate handling is difficult.

Contrary to this, in the embodiment of the present invention, the prescribed prism amount APL is determined within the prism prescription range between the prism amount in the horizontal direction of the first prism amount APF0H and the prism amount in the horizontal direction of the second prism amount APN0H as well as within the prism prescription range between the first prism amount in the vertical direction APF0V and the second prism amount in the vertical direction APN0V. Therefore, supposing that the prism amount in the horizontal direction of the first prism amount APF0H is 4Δ (prism diopter) and the prism amount in the horizontal direction of the second prism amount APN0H is 2Δ, the prescribed prism amount in the horizontal direction APLH is determined within a prescription range between 2Δ and 4Δ. A prescription range of a prism in the vertical direction is similar to the above. Furthermore as for the allocation within this prescription range, the allocation is obtained, from the information related to life scenes where the spectacle wearer plans to use the spectacle lens, based on the importance indices based on a life style of the spectacle wearer. This allows for determining the prescribed prism amount in the horizontal direction APLH and the prescribed prism amount in the vertical direction APLV in the allocation appropriate for the life style of the spectacle wearer. Hereinafter, the examples will be described.

Example 1

When importance of distance vision and near vision is equivalent in a life style of the spectacle wearer, the value of KF in the above mathematical formula equals 0.5 while the value of KN equals 0.5. According to the mathematical formula 2, when the aligning prism amount in the horizontal direction APF0H in distance vision equals 3Δ, a value of APF1H equals 1.5Δ. When the aligning prism amount in the horizontal direction APN0H in near vision equals 2Δ, a value of APN1H equals 1Δ. As a result of this, the prescribed prism amount in the horizontal direction APLH is determined as 2.5Δ. Similarly with the aligning prism in the vertical direction, when the aligning prism amount in the vertical direction APF0V in distance vision equals 1Δ, a value of APF1V equals 0.5Δ. When the aligning prism amount in the vertical direction APN0V in near vision equals 0.5Δ, a value of APN1V equals 0.25Δ. As a result of this, the prescribed prism amount in the vertical direction APLV is determined as 0.75Δ.

This prescribed prism amount in the horizontal direction APLH is within the prism prescription range between the first prism amount in the horizontal direction APF0H of 3Δ and the second prism amount in the horizontal direction APN0H of 2Δ and is a value exactly in the middle. Furthermore, the prescribed prism amount in the vertical direction APLV is within the prism prescription range between the first prism amount in the vertical direction APF0V of 1Δ and the second prism amount in the vertical direction APN0V of 0.5Δ and is a value exactly in the middle. This results as a prescribed prism amount suitable for the life style of the spectacle wearer with equivalent importance for distance vision and near vision.

Example 2

When importance of distance vision is relatively high in a life style of the spectacle wearer, the value of KF in the above mathematical formula equals 0.7 while the value of KN equals 0.3 for example. According to the mathematical formula 2, when the aligning prism amount in the horizontal direction APF0H in distance vision equals 3Δ, a value of APF1H equals 2.1Δ. When the aligning prism amount in the horizontal direction APN0H in near vision equals 2Δ, a value of APN1H equals 0.6Δ. As a result of this, the prescribed prism amount in the horizontal direction APLH is determined as 2.7Δ. Similarly with the aligning prism in the vertical direction, when the aligning prism amount in the vertical direction APF0V in distance vision equals 1Δ, a value of APF1V equals 0.7Δ. When the aligning prism amount in the vertical direction APN0V in near vision equals 0.5Δ, a value of APN1V equals 0.15Δ. As a result of this, the prescribed prism amount in the vertical direction APLV is determined as 0.85Δ.

This prescribed prism amount in the horizontal direction APLH is within the prism prescription range between the first prism amount in the horizontal direction APF0H of 3Δ and the second prism amount in the horizontal direction APN0H of 2Δ and is a value closer to the first prism amount in the horizontal direction (prism amount measured with distance vision) APF0H. Furthermore, this prescribed prism amount in the vertical direction APLV is within the prism prescription range between the first prism amount in the vertical direction APF0V of 1Δ and the second prism amount in the vertical direction APN0V of 0.5Δ and is a value closer to the first prism amount in the vertical direction (prism amount measured with distance vision) APF0V. This results as a prescribed prism amount suitable for the life style of the spectacle wearer with relatively higher importance for distance vision.

Example 3

When importance of near vision is relatively high in a life style of the spectacle wearer, the value of KF in the above mathematical formula equals 0.2 while the value of KN equals 0.8 for example. According to the mathematical formula 2, when the aligning prism amount in the horizontal direction APF0H in distance vision equals 3Δ, a value of APF1H equals 0.6Δ. When the aligning prism amount in the horizontal direction APN0H in near vision equals 2Δ, a value of APN1H equals 1.6Δ. As a result of this, the prescribed prism amount in the horizontal direction APLH is determined as 2.2Δ. Similarly with the aligning prism in the vertical direction, when the aligning prism amount in the vertical direction APF0V in distance vision equals 1Δ, a value of APF1V equals 0.2Δ. When the aligning prism amount in the vertical direction APN0V in near vision equals 0.5Δ, a value of APN1V equals 0.4Δ. As a result of this, the prescribed prism amount in the vertical direction APLV is determined as 0.6Δ.

This prescribed prism amount in the horizontal direction APLH is within the prism prescription range between the first prism amount in the horizontal direction APF0H of 3Δ and the second prism amount in the horizontal direction APN0H of 2Δ and is a value closer to the second prism amount in the horizontal direction (prism amount measured by near vision) APN0H. Furthermore, this prescribed prism amount in the vertical direction APLV is within the prism prescription range between the first prism amount in the vertical direction APF0V of 1Δ and the second prism amount in the vertical direction APN0V of 0.5Δ and is a value closer to the second prism amount in the vertical direction (prism amount measured with near vision) APN0V.

This results as a prescribed prism amount suitable for the life style of the spectacle wearer with relatively higher importance for near vision.

5. Other Embodiments

Hereinafter, other embodiments of the present invention will be described.

In this embodiment, specific contents of information related to life scenes of a spectacle wearer input for determining a prescribed prism amount and a method to determine the prescribed prism amount based on this information are different as compared to the aforementioned embodiment.

First, as for the information related to life scenes of the spectacle wearer, a coefficient K (where $0 \leq K \leq 1.0$ is satisfied) corresponding to a life style of the spectacle wearer is input from an inputter 5. The coefficient K is a weighting coefficient for determining the prescribed prism amount according to the life style of the spectacle wearer. This coefficient K is only required to be input from the inputter 5 by a store clerk at an optician's store or more preferably by a qualified person such as an ophthalmologist or an optometrist after confirming usage of a spectacle lens by the spectacle wearer and considering the contents thereof.

Furthermore, a determiner 11 determines a prism amount for correcting fixation disparity from the following formula 1 where, as described above, an aligning prism amount in the horizontal direction for correcting fixation disparity is denoted as APLH, an aligning prism amount in the vertical direction is denoted as APLV, the first prism amount in the horizontal direction is denoted as APF0H, the second prism amount in the horizontal direction is denoted as APN0H, the first prism amount in the vertical direction is denoted as APF0V, and the second prism amount in the vertical direction is denoted as APN0V.

$$APLH = APF0H*(1-K) + APN0H*K$$

$$APLV = APF0V*(1-K) + APN0V*K \quad \text{[Formula 1]}$$

Employing such a configuration allows for determining the prescribed prism amount in accordance with the life style of the spectacle wearer and providing a spectacle lens with prism prescription based thereon.

That is, when importance of distance vision and near vision is equivalent to each other in the life style of the spectacle wearer, inputting the coefficient K of 0.5 according to the life style allows for providing the spectacle lens with prescription prism suitable for the life style of the spectacle wearer in whose life style importance of distance vision and near vision is equivalent to each other. Alternatively, when importance of distance vision is relatively higher in the life style of the spectacle wearer, inputting the coefficient K of a value less than 0.5 according to the life style allows for providing the spectacle lens with prescription prism suitable for the life style of the spectacle wearer in whose life style importance of distance vision is relatively higher. Alternatively, when importance of near vision is relatively higher in the life style of the spectacle wearer, inputting the coefficient K of a value larger than 0.5 allows for providing the spectacle lens with prescription prism suitable for the life style of the spectacle wearer in whose life style importance of near vision is relatively higher.

Note that the value of the coefficient K may be input according to the following criteria other than inputting a value according to the life style of the spectacle wearer. That is, when the spectacle wearer with fixation disparity eliminates fixation disparity by wearing a spectacle lens, elimination of fixation disparity of near vision is usually regarded as more important than elimination of fixation disparity of distance vision. This is because, when the spectacle wearer looks at an object through the spectacle lens, the spectacle wearer feels that a vision is uncomfortable due to fixation disparity more in near vision than in distance vision. Therefore, it is desirable to regard near vision as more important and to input, as the value of the coefficient K, a value larger than 0.5, specifically a value such as 0.75. Furthermore upon inputting the coefficient K, an input value of the coefficient K may be adjusted (added or reduced) according to the life style of the spectacle wearer with a reference of K=0.75.

Incidentally, a range of the value of the coefficient K is $0 \leq K \leq 1.0$ in the above example; however, the value of the coefficient K may be set such that the aligning prism amount to be obtained from the formula 1 does not equal to the first prism amount nor to the second prism amount (for example $0<K<1.0$).

6. Variations

A technical scope of the present invention is not limited to the aforementioned embodiments but may include various modifications or improvements as long as the specific effects obtained by the elements of the present invention or a combination thereof can be derived.

For example in the above embodiment, six life scenes are shown as an example where the importance indices based on the life style of the spectacle wearer are classified into three ranks for each of the life scenes and thereby input; however, the number of life scenes or the number of ranks of importance indices to input may be changed as appropriate. Moreover, the information related to the life scenes is quite preferable as the information used for allocation of the first prism amount and the second prism amount; however, other information may be employed. For example allocation amounts of the first prism amount and the second prism amount may be determined according to a hobby or occupation of the spectacle wearer.

Also in the above embodiment, the case where the prism amount measured in distance vision (first prism amount) and the prism amount measured in near vision (second prism amount) are input has been described as an example of the measurement information input by the measurement information input section; however, the measurement information is not limited thereto. That is, apart from the case of inputting the prism amount measured with distance vision and the prism amount measured with near vision as measurement information, a fixation disparity amount of the spectacle wearer may be directly measured and thereby a fixation disparity amount measured with distance vision (first fixation disparity amount) and a second fixation disparity amount measured with near vision may be input without measuring the aligning prism for correcting fixation disparity. When inputting the fixation disparity amount as the measurement information, obtaining the prism amount by calculation from the input fixation disparity amount allows for defining the prism prescription range.

Incidentally, as for a method to obtain the prism amount by calculation from the fixation disparity amount, the prism amount may be obtained assuming that relation between the fixation disparity amount and the prism amount is proportional. Alternatively, relation between the prism amount and the prism amount may be empirically grasped on a plurality of subjects and the prism amount may be obtained based on this relation.

Moreover, data input of the fixation disparity amount may be performed by, for example displaying an input screen as illustrated in FIG. 6 on the display 7, thereby allowing an operator (store clerk at an optician's store or the like) to select entry fields 31 and 32 for the fixation disparity amount with a mouse or the like in order while looking at this input screen and to input corresponding data with a keyboard or the like. A distance vision fixation disparity amount in FIG. 6 corresponds to the first fixation disparity amount obtained from calculation based on the first prism amount APF0 obtained by measuring the prism amount of the spectacle wearer at the eye examination distance corresponding to distance vision and a near vision fixation disparity amount in FIG. 6 corresponds to the second fixation disparity amount obtained from calculation based on the second prism amount APN0 obtained by measuring the prism amount of the spectacle wearer at the eye examination distance corresponding to near vision.

The outputter 12 also outputs, to the display 7, the recommended type of spectacle lens in order to present the recommended type of spectacle lens to the spectacle wearer in the above embodiment the, thereby displaying the recommended type on a screen of the display 7; however, the present invention is not limited thereto. For example, the outputter 12 may output the recommended type of spectacle lens to a printing device such as a printer, thereby printing the recommended type on a paper or the like. Other than the above, the outputter 12 may transmit the recommended type of spectacle lens to a portable information terminal other than the order placing device 2 by wireless communication or the like, thereby displaying the recommended type on a display screen of the portable information terminal.

Furthermore, the case where calculation of the aligning prism amount for correcting fixation disparity is performed in the order placing device 2 has been described in the above embodiment; however, the present invention is not limited thereto. For example the calculation may be performed in the order receiving device 3 or by a server (e.g. data server) (not illustrated) connected to the communication network 4. When the calculation is performed in the order receiving device 3, the first prism amount and the second prism amount may be input by the inputter 5 of the order placing device 2 and transmitted to the order receiving device 3, whereupon the order receiving device 3 may calculate the aligning prism amount for correcting fixation disparity and a calculation result thereof may be transmitted to the order placing device 2.

Incidentally, the aforementioned method to obtain the prism amount by calculation from the fixation disparity amount may be implemented by the order receiving device 3 or another configuration.

Furthermore, the eye examination distance corresponding to distance vision and the eye examination distance corresponding to near vision are employed in the above embodiment; however, the present invention is not limited thereto. For example, an eye examination distance corresponding to intermediate vision for looking at a distance between the distance vision and the near vision and the eye examination distance corresponding to near vision may be employed. A spectacle lens in this case is usually called an "intermediate-near vision lens". In this case, the above two distances can be expressed as a "first distance" and a "second distance shorter than the first distance" in the above embodiment.

Meanwhile, specific examples of obtaining the aligning prism amount of the intermediate-near vision lens include the following. For example, assuming the eye examination distance corresponding to intermediate vision to be a distance of 80 cm between a PC display and a spectacle wearer, a first prism amount in that distance is obtained. In addition to this, assuming the eye examination distance corresponding to near vision to be a distance of 40 cm between a keyboard and the spectacle wearer, a second prism amount in that distance is obtained. Thereafter, allocation of the first and the second prism amounts is determined based on the information related to the life scene (for example, first prism amount:second prism amount=70:30).

Furthermore, the first and the second prism amounts are separately obtained for each of the two distances in the above example; however, a third distance may also be set. For example, prism amounts may be obtained corresponds to three distances of the eye examination distance corresponding to distance vision, an eye examination distance corresponding to intermediate vision, and the eye examination distance corresponding to near vision. In this case, the eye examination distance corresponding to distance vision corresponds to the first distance with the eye examination distance corresponding to near vision corresponding to the second distance and the eye examination distance corresponding to intermediate vision corresponding to the third distance.

Weighting may be then performed on the first, the second, and a third prism amounts and an aligning prism amount to be uniformly included in a spectacle lens for correction of fixation disparity may be determined within a prism prescription range between the first prism amount and the second prism amount.

REFERENCE SIGNS LIST 1 spectacle lens supply system
2 order placing device
3 order receiving device
4 communication network
5 inputter
6 computer section
7 display
11 determiner
12 outputter
13 order placing processor
14 storage

The invention claimed is:

1. A spectacle lens supply system to supply a spectacle lens for correcting fixation disparity of a spectacle wearer, of a spectacle lens, having the fixation disparity, the system comprising:
  a determination section to determine an aligning prism amount to be uniformly included in the spectacle lens for correcting the fixation disparity, based on a first aligning prism amount obtained by measurement at an eye examination distance corresponding to a first distance, a second aligning prism amount obtained by measurement at an eye examination distance corresponding to a second distance shorter than the first distance, and information used for allocation of the first aligning prism amount and the second aligning prism amount, within a prism prescription range between the first aligning prism amount and the second aligning prism amount.

2. The spectacle lens supply system according to claim 1, wherein the information used for allocation of the first aligning prism amount and the second aligning prism amount relates to a life scene where the spectacle wearer plans to use the spectacle lens.

3. The spectacle lens supply system according to claim 2, the system comprising:
  a measurement information input section to input the first aligning prism amount and the second aligning prism amount; and
  a life scene information input section to input the information related to the life scene.

4. The spectacle lens supply system according to claim 3, the system further comprising a display to display an input screen for inputting the first aligning prism amount and the second aligning prism amount.

5. The spectacle lens supply system according to claim 3, wherein the life scene information input section inputs information representing an importance index based on a life style of the spectacle wearer for each of a plurality of life scenes prepared in advance, and
  the determination section obtains allocation within the prism prescription range using the importance index for each of the plurality of life scenes input by the input section and determines an aligning prism amount for correcting the fixation disparity according to this allocation.

6. The spectacle lens supply system according to claim 3, wherein the life scene information input section inputs, as the information related to the life scene, a coefficient K (where 0<K<1.0 is satisfied) corresponding to a life style of the spectacle wearer, and the determination section determines an aligning prism amount for correcting the fixation disparity from the following formula 1 where a prism amount in a horizontal direction of the aligning prism amount for correcting the fixation disparity is denoted as APLH, a prism amount in a vertical direction thereof is denoted as APLV, a prism amount in the horizontal direction of the first aligning prism amount is denoted as APFOH, a prism amount in the vertical direction of the first aligning prism amount is denoted as APFOV, a prism amount in the horizontal direction of the second aligning prism amount is denoted as APNOH, and a prism amount in the vertical direction of the second aligning prism amount is denoted as APNOV $$APLH=APFOH*(1-K)+APNOH*KAPLV=APFOV*(1-K)+APNOV*K.$$ [Formula 1]

7. The spectacle lens supply system according to claim 1, wherein the first distance is an eye examination distance corresponding to distance vision and the second distance is an eye examination distance corresponding to near vision.

8. A non-transitory computer-readable recording medium that stores a computer program for a spectacle lens supply system instructing that, when executed by a computer, causes the computer:
  to determine an aligning prism amount for correcting a fixation disparity of a spectacle wearer, of a spectacle lens, when a first aligning prism amount obtained by measurement at an eye examination distance corresponding to a first distance, a second aligning prism amount obtained by measurement at an eye examination distance corresponding to a second distance shorter than the first distance, and information used for allocation of the first aligning prism amount and the second aligning prism amount are input, based on the input information within a prism prescription range between the first aligning prism amount and the second aligning prism amount.

9. A method for producing a spectacle lens for correcting fixation disparity of a spectacle wearer, of a spectacle lens, having the fixation disparity, the method comprising the steps of:
    determining an aligning prism amount for correcting the fixation disparity, based on a first aligning prism amount obtained by measurement at an eye examination distance corresponding to a first distance, a second aligning prism amount obtained by measurement at an eye examination distance corresponding to a second distance shorter than the first distance, and information used for allocation of the first aligning prism amount and the second aligning prism amount, within a prism prescription range between the first aligning prism amount and the second aligning prism amount; and
    producing a spectacle lens uniformly including the determined aligning prism amount for correcting the fixation disparity.

10. A prism amount determination device to determine a prism amount for correcting fixation disparity of a spectacle wearer, of a spectacle lens, having the fixation disparity, the device comprising:
    a determination section to determine an aligning prism amount to be uniformly included in the spectacle lens for correcting the fixation disparity, based on a first aligning prism amount obtained by measurement at an eye examination distance corresponding to a first distance, a second aligning prism amount obtained by measurement at an eye examination distance corresponding to a second distance shorter than the first distance, and information used for allocation of the first aligning prism amount and the second aligning prism amount, within a prism prescription range between the first aligning prism amount and the second aligning prism amount.

11. A prism amount determination method to determine an aligning prism amount for correcting fixation disparity of a spectacle wearer, of a spectacle lens, having the fixation disparity, the method comprising the step of:
    determining an aligning prism amount for correcting the fixation disparity, based on a first aligning prism amount obtained by measurement at an eye examination distance corresponding to a first distance, a second aligning prism amount obtained by measurement at an eye examination distance corresponding to a second distance shorter than the first distance, and information used for allocation of the first aligning prism amount and the second aligning prism amount, within a prism prescription range between the first aligning prism amount and the second aligning prism amount.

\* \* \* \* \*